(12) United States Patent
Bédard et al.

(10) Patent No.: US 7,314,490 B2
(45) Date of Patent: *Jan. 1, 2008

(54) ACTUATED LEG PROSTHESIS FOR ABOVE-KNEE AMPUTEES

(75) Inventors: Stéphane Bédard, Saint-Augustin-de-Desmaures (CA); Pierre-Olivier Roy, Sainte-Foy (CA)

(73) Assignee: Victhom Human Bionics Inc., Saint-Augustin-de-Desmaures, (Quebec) (CA)

( * ) Notice: Subject to any disclaimer, the term of this patent is extended or adjusted under 35 U.S.C. 154(b) by 92 days.

This patent is subject to a terminal disclaimer.

(21) Appl. No.: 10/463,495

(22) Filed: Jun. 17, 2003

(65) Prior Publication Data

US 2004/0111163 A1 Jun. 10, 2004

Related U.S. Application Data

(60) Provisional application No. 60/453,556, filed on Mar. 11, 2003, provisional application No. 60/424,261, filed on Nov. 6, 2002, provisional application No. 60/405,281, filed on Aug. 22, 2002.

(51) Int. Cl.
*A61F 2/64* (2006.01)
*A61F 2/70* (2006.01)

(52) U.S. Cl. .......................................... 623/24; 623/39
(58) Field of Classification Search ............ 623/24–26, 623/39–46
See application file for complete search history.

(56) References Cited

U.S. PATENT DOCUMENTS

| 4,179,759 | A | 12/1979 | Smith |
| 4,521,924 | A | 6/1985 | Jacobsen et al. |
| 4,994,086 | A | 2/1991 | Edwards |
| 5,062,856 | A | 11/1991 | Sawamura et al. |
| 5,062,857 | A | 11/1991 | Berringer et al. |
| 5,133,773 | A | 7/1992 | Sawamura et al. |
| 5,133,774 | A | 7/1992 | Sawamura et al. |
| 5,252,102 | A | 10/1993 | Singer et al. |
| 5,383,939 | A | 1/1995 | James |

(Continued)

FOREIGN PATENT DOCUMENTS

EP 0 549 855 A2 7/1993

(Continued)

OTHER PUBLICATIONS

Flowers et al., Journal of Biomechanical Engineering: Transactions of the ASME; Feb. 1977, pp. 3-8.*

(Continued)

*Primary Examiner*—David H. Willse
(74) *Attorney, Agent, or Firm*—Devine, Millimet & Branch; Paul C. Remus; Raymond I. Bruttomesso, Jr.

(57) ABSTRACT

The actuated leg prosthesis comprises a knee member, a socket connector provided over the knee member, an elongated trans-tibial member having a bottom end under which is connected an artificial foot, and a linear actuator. A first pivot assembly allows to operatively connect the trans-tibial member to the knee member. A second pivot assembly allows to operatively connect an upper end of the actuator to the knee member. A third pivot assembly allows to operatively connect a bottom end of the actuator to the bottom end of the trans-tibial member. The prosthesis can be provided as either a front actuator configuration or a rear actuator configuration.

24 Claims, 11 Drawing Sheets

U.S. PATENT DOCUMENTS

| | | |
|---|---|---|
| 5,443,528 A | 8/1995 | Allen |
| 5,571,205 A | 11/1996 | James |
| 5,571,213 A | 11/1996 | Allen |
| 5,650,704 A | 7/1997 | Pratt et al. |
| 5,704,946 A | 1/1998 | Greene |
| 5,746,774 A | 5/1998 | Kramer et al. |
| 5,779,735 A | 7/1998 | Molino |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Conner |
| 6,007,582 A | 12/1999 | May |
| 6,113,642 A | 9/2000 | Petrofsky et al. |
| 6,361,570 B1 | 3/2002 | Gow |
| 6,425,926 B1 | 7/2002 | Grundel |
| 6,494,039 B2 | 12/2002 | Pratt et al. |
| 2001/0029400 A1 | 10/2001 | Deffenbaugh et al. |
| 2002/0052663 A1 | 5/2002 | Herr et al. |
| 2004/0064195 A1* | 4/2004 | Herr .......................... 623/24 |
| 2004/0193286 A1 | 9/2004 | Grundel |

FOREIGN PATENT DOCUMENTS

| | | |
|---|---|---|
| EP | 1 166 726 A1 | 1/2002 |
| EP | 1 169 982 A1 * | 1/2002 |
| FR | 2623086 | 5/1989 |
| GB | 2 260 495 A * | 4/1993 |
| JP | 11056885 | 3/1999 |
| JP | 2001277175 | 10/2001 |
| WO | WO96/41599 | 12/1996 |
| WO | WO99/08621 | 2/1999 |
| WO | WO 99/08621 | 2/1999 |

OTHER PUBLICATIONS

English translation of JP 2002-191654 A.*
EPO—International Search Report, Dec. 5, 2003: PCT/CA03/00902.
Dietl, H., Der Einsatz von Elektronik bei Prothesen zur Versorgung der unteren Extremitat, Med. Orth. Tech. 117 (1997) 31-35.
Australian Search Report, Nov. 25, 2005.

* cited by examiner

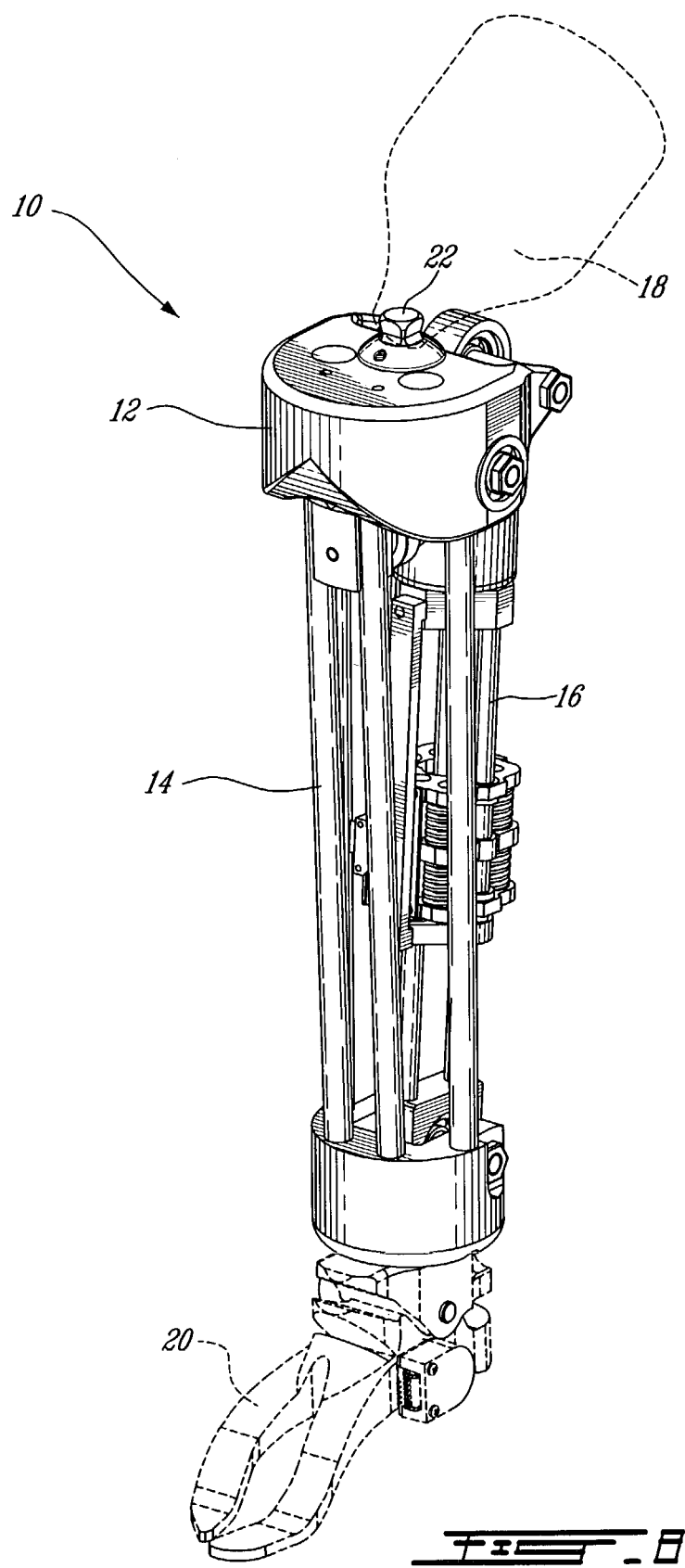

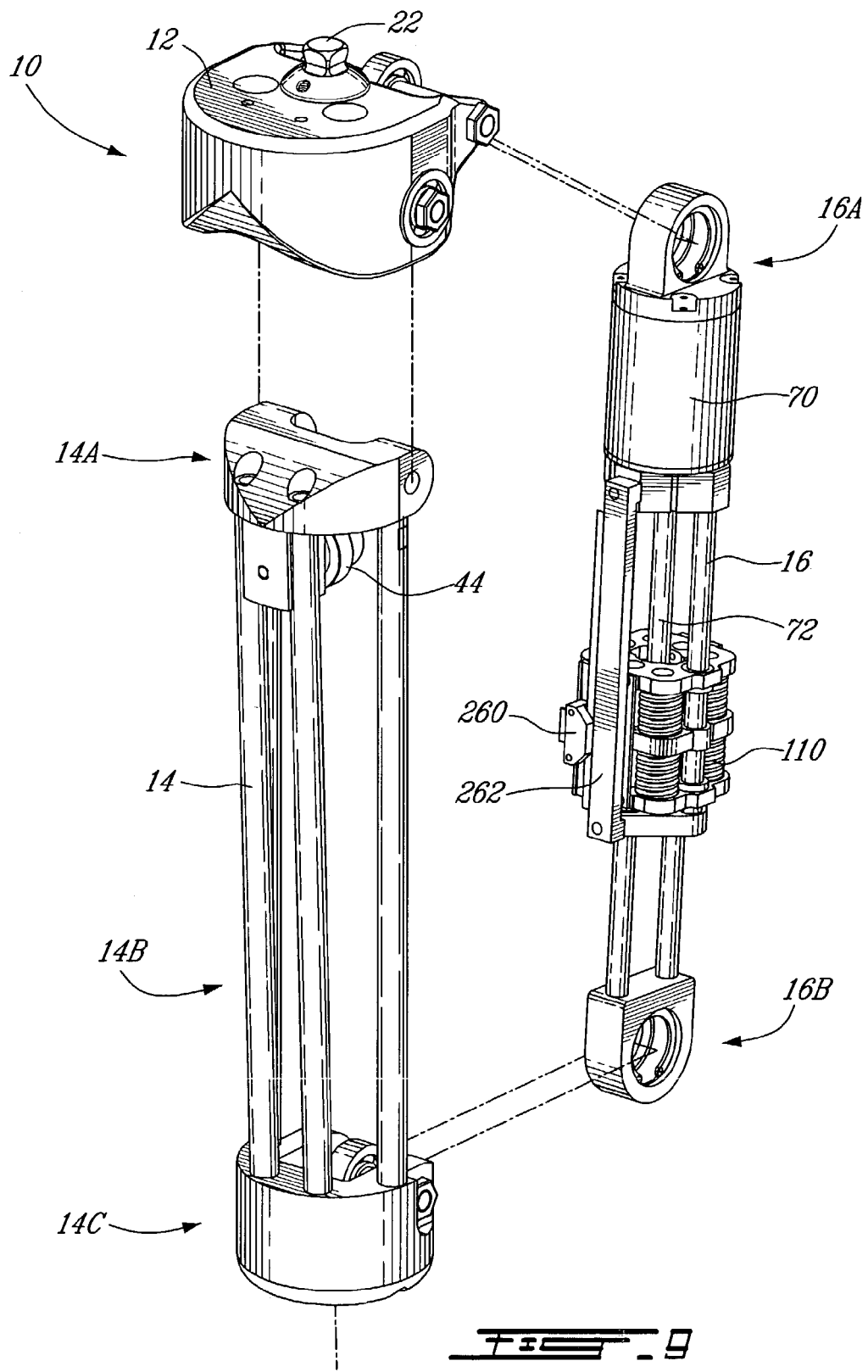

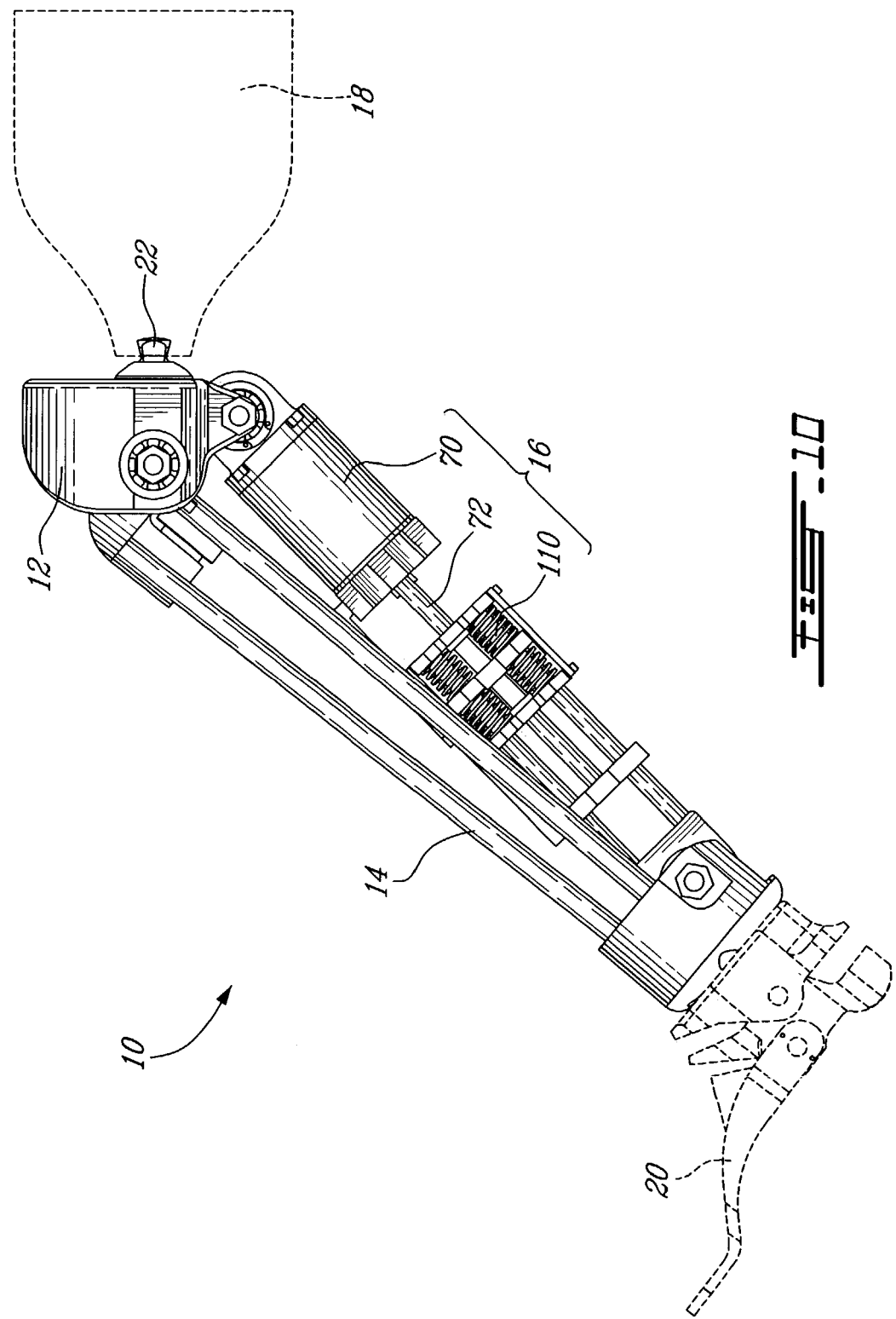

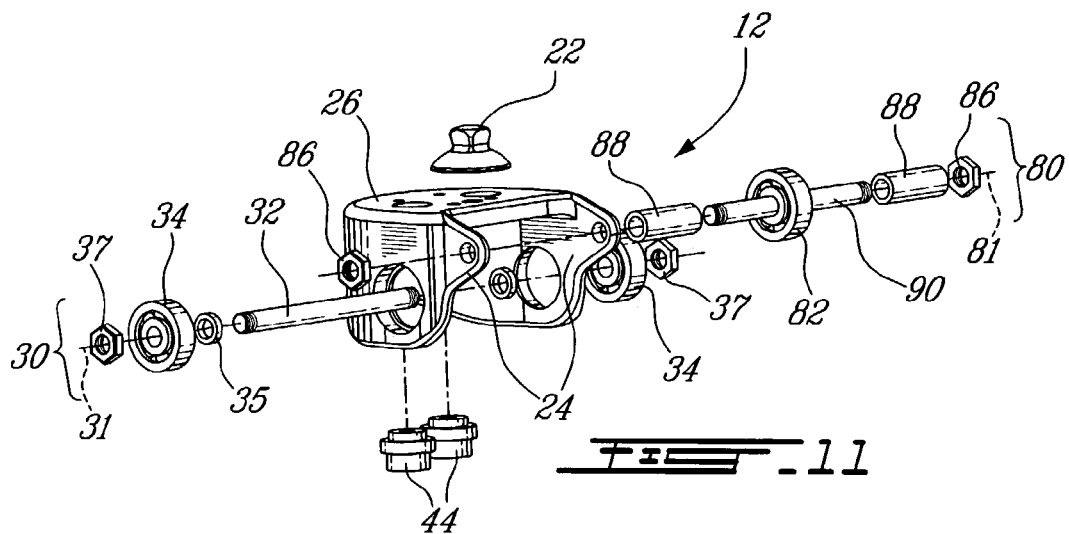
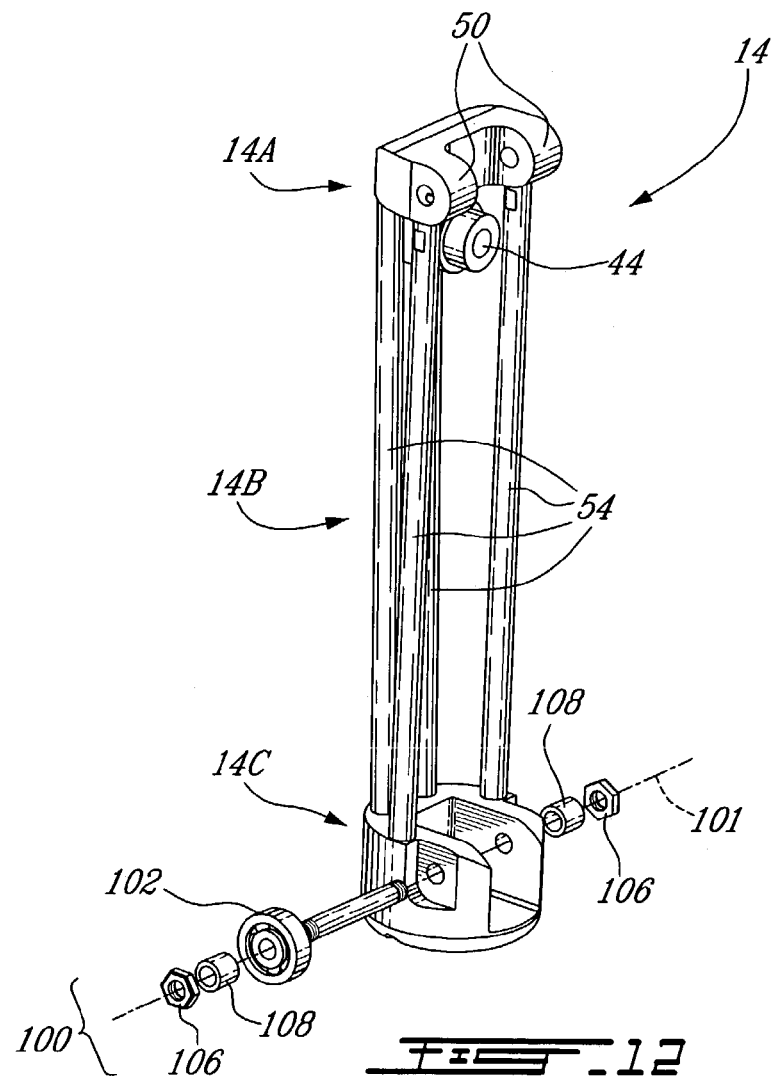

ACTUATED LEG PROSTHESIS FOR ABOVE-KNEE AMPUTEES

CROSS-REFERENCE TO RELATED APPLICATIONS

The present application claims the benefits of U.S. provisional patent applications No. 60/405,281 filed Aug. 22, 2002; No. 60/424,261 filed Nov. 6, 2002; and No. 60/453,556 filed Mar. 11, 2003, all of which are hereby incorporated by reference.

TECHNICAL FIELD

The present invention relates to an actuated leg prosthesis for above-knee amputees.

BACKGROUND

Over the years, many kinds of leg prostheses have been devised in effort to replace the leg or legs that amputees have lost. All these leg prostheses have the difficult task of giving to these amputees a life as normal as possible. The complexity of human locomotion, however, is such that conventional leg prostheses have until now only been using passive mechanisms in the most sophisticated available devices. Conventional leg prostheses are very limited compared to a real human leg and some needs were thus not entirely fulfilled by them.

According to amputees, specific conditions of use of conventional leg prostheses, such as repetitive movements and continuous loading, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

Another problem is that during the amputees' locomotion, energy used for moving the prosthesis mainly originates from the amputees themselves because conventional leg prostheses do not have self-propulsion capabilities. This has considerable short and long-term negative side effects. Recent developments in the field of energy-saving prosthetic components have partially contributed to improve energy transfer between the amputees and their prosthesis. Nevertheless, the problem of energy expenditure is still not fully resolved and remains a major concern.

A further problem is that the dynamic role played by the stump during the amputees' locomotion renders difficult the prolonged wearing of conventional leg prostheses. This may create, among other things, skin problems such as folliculitis, contact dermatitis, oedema, cysts, skin shearing, scarring and ulcers. Although these skin problems may be partially alleviated by using a silicon sheath, a complete suction socket or powder, minimizing these skin problems remain a concern.

Considering this background, it clearly appears that there was a need to develop improved leg prosthesis for above-knee amputees.

SUMMARY

In accordance with a first broad aspect of the present invention, there is provided an improved actuated leg prosthesis comprising a knee member, first means for connecting a socket over the knee member, an elongated trans-tibial member, second means for connecting an artificial foot under a bottom end of the trans-tibial member, a linear actuator, third means for operatively connecting the trans-tibial member to the knee member, fourth means for operatively connecting the upper end of the actuator to the knee member, and fifth means for operatively connecting the bottom end of the actuator to the bottom end of the trans-tibial member.

In accordance with another broad aspect of the present invention, there is provided an improved actuated leg prosthesis comprising a knee member, a socket connected over the knee member, an elongated trans-tibial member, an artificial foot connected under a bottom end of the trans-tibial member, and a linear actuator. A first pivot assembly allows to operatively connect the trans-tibial member to the knee member. The first pivot assembly defines a first pivot axis that is perpendicular to a main longitudinal axis of the trans-tibial member. A second pivot assembly allows to operatively connect an upper end of the actuator to the knee member. The second pivot assembly defines a second pivot axis that is substantially parallel to the first pivot axis. The second pivot axis is also spaced apart from the first pivot axis and the main longitudinal axis. A third pivot assembly allows to operatively connect a bottom end of the actuator to the bottom end of the trans-tibial member. The third pivot assembly defines a third pivot axis that is substantially parallel to and spaced apart from the first pivot axis.

These and other aspects of the present invention are described in or apparent from the following detailed description, which description is made in conjunction with the accompanying figures.

BRIEF DESCRIPTION OF THE FIGURES

FIG. 8 is a perspective view of an actuated prosthesis with a rear actuator configuration, in accordance with another possible embodiment of the present invention.

FIG. 9 is a partially exploded perspective view of the prosthesis shown in FIG. 8.

FIG. 10 is a side view of the prosthesis shown in FIG. 8.

FIG. 11 is an exploded perspective view of the knee member, the first pivot assembly and the second pivot assembly shown in FIG. 8.

FIG. 12 is a partially exploded view of the trans-tibial member and the third pivot assembly shown in FIG. 8.

DETAILED DESCRIPTION

The appended figures show an actuated prosthesis (10) in accordance with the preferred embodiment and an alternate embodiment of the present invention. It should be understood that the present invention is not limited to these illustrated implementations since various changes and modifications may be effected herein without departing from the scope of the appended claims.

The prosthesis (10) has two main configurations, one being a front actuator configuration and the other being a rear actuator configuration. The front actuator configuration is preferred. FIGS. 1 to 7 show the prosthesis (10) with the front actuator configuration while FIGS. 8 to 13 show the prosthesis (10) with the rear actuator configuration.

Front Actuator Configuration

Figure 1:
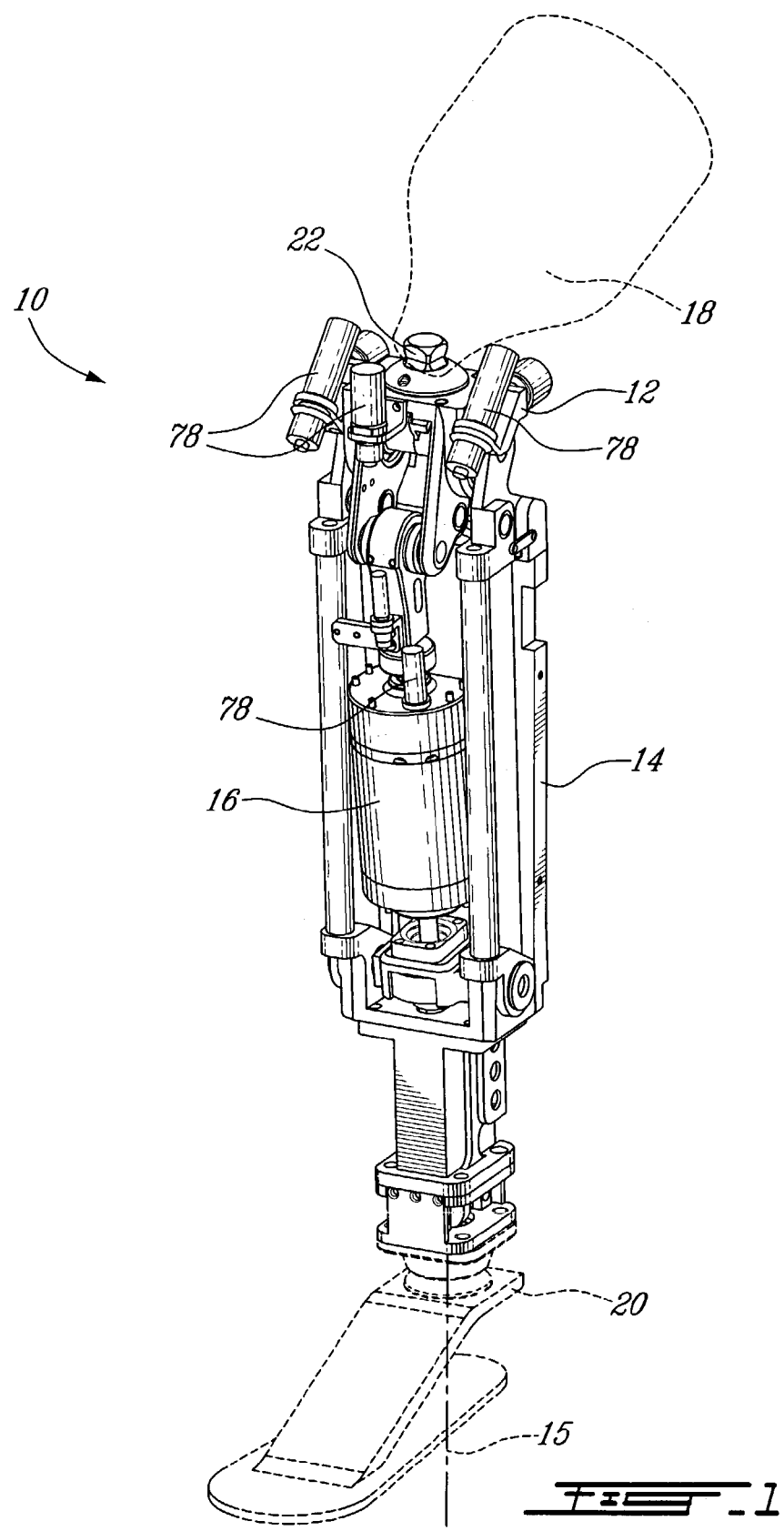
FIG. 1 is a perspective view of an actuated prosthesis with a front actuator configuration, in accordance with the preferred embodiment of the present invention.
Figure 2:
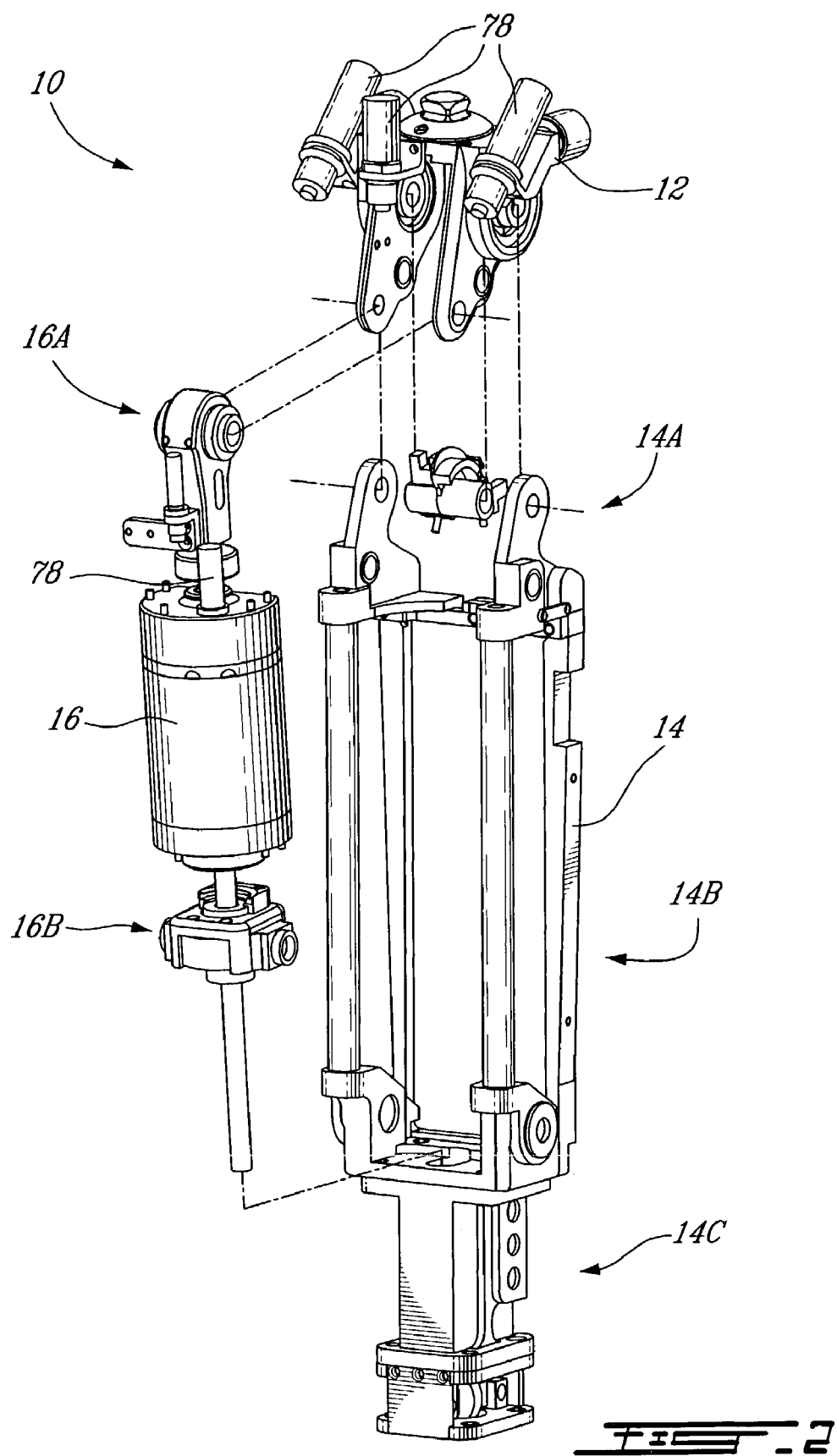
FIG. 2 is a partially exploded perspective view of the prosthesis shown in FIG. 1.

FIGS. 1 and 2 show the basic components of the prosthesis (10), which include a knee member (12), an elongated trans-tibial member (14), and a linear actuator (16) set between the knee member (12) and the trans-tibial member (14). The prosthesis (10) also comprises means for connecting a socket (18) on the knee member (12) and means for connecting an artificial foot (20) under a bottom end of the trans-tibial member (14).

The socket (18) must achieve adequate effort transfers between the prosthesis (10) and the amputee's stump. The design of the socket (18) is usually a custom operation in order to achieve an optional load transmission, stability and efficient control for the stump's mobility. The socket (18) is generally held in place on the stump of the user by a suction effect created by an appropriate system such as, for example, a flexible suction liner of type "Thermolyn" manufactured by the Otto Bock Inc. The prosthesis (10) can otherwise use any suitable sockets available on the market.

The means for connecting the socket (18) may comprise a bottom socket connector (22) provided over the knee member (12). The bottom socket connector (22) is preferably removably connected by means of fasteners, for instance screws or bolts. The exact type of bottom socket connector (22) may vary. An example is a connector having a standard male pyramid configuration, such as male pyramid model 4R54 manufactured by Otto Bock Inc. Another example is the sliding connector with male pyramid model 2054-2 manufactured by Ossur Inc. The socket (18) would then be equipped with a corresponding upper connector which fits over the bottom male connector (22). Other types of connectors may be used as well.

The knee member (12) ensures the junction between the socket (18) and the trans-tibial member (14) with at least one degree of freedom in rotation. The knee member (12) range of motion is preferably about 105 degrees, where zero degree is at full extension and 105 degrees is at maximal knee flexion.

Figure 3:
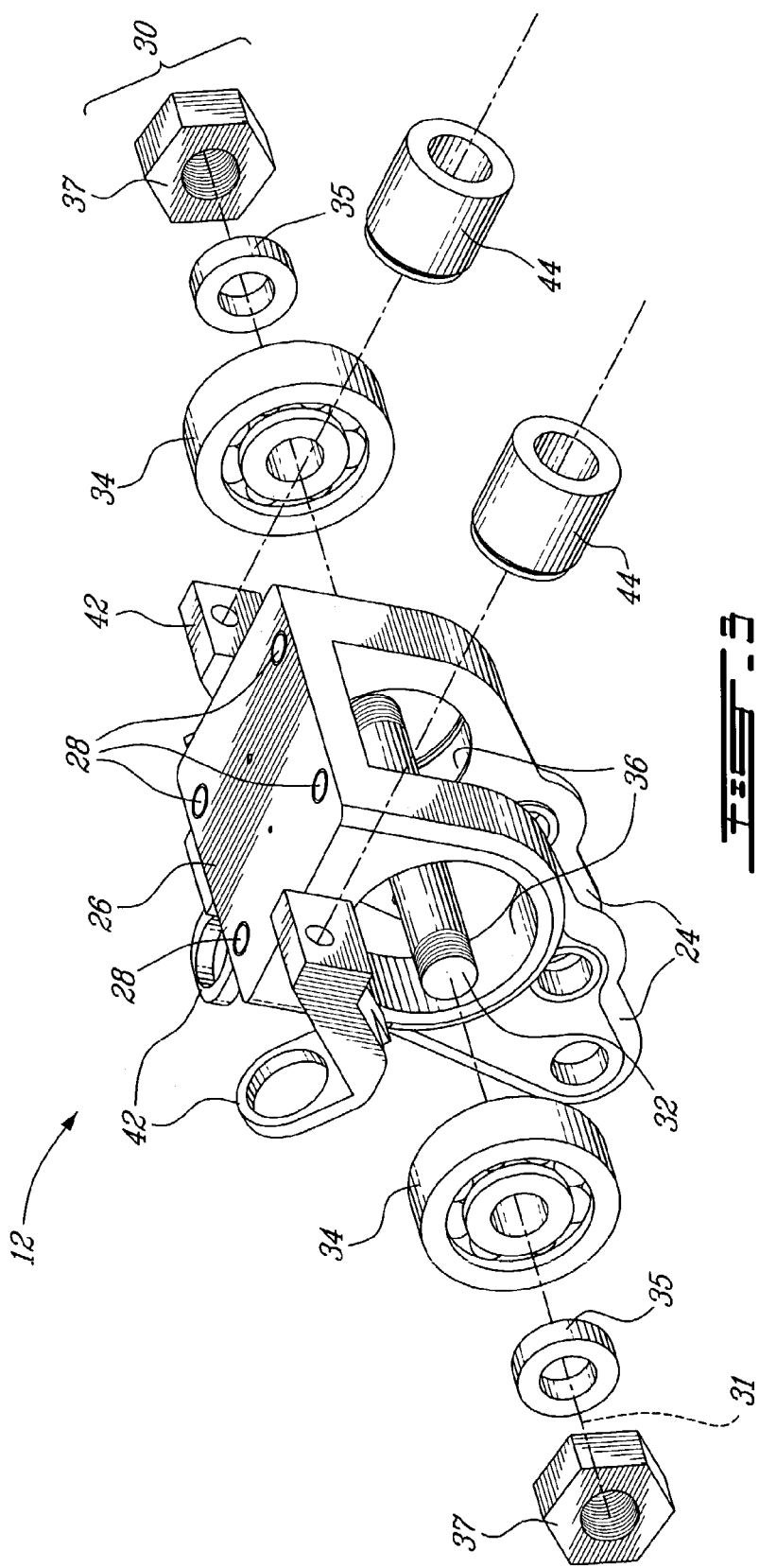
FIG. 3 is an exploded perspective view of the knee member and the first pivot assembly shown in FIG. 1.

FIG. 3 shows an enlarged view of the knee member (12). The knee member (12) is preferably a fork-shaped item, with two flanges (24) projecting from an upper plate (26). The upper plate (26) includes four threaded holes (28) for the removable fasteners of the bottom socket connector (22).

The knee member (12) in the preferred embodiment is connected to the trans-tibial member (14) by means of a first pivot assembly (30). The first pivot assembly (30) allows to operatively connect the trans-tibial member (14) to the knee member (12), thereby making possible a relative rotation between these two parts. It should be noted that the first pivot assembly (30) can also be polycentric. This means that the movement between the knee member (12) and the trans-tibial member (14) is not purely rotational but follows a much more complex pattern. The right and left sides of the parts can further be slightly different, thereby causing a slight torsion movement around a vertical axis. Nevertheless, the general overall movement remains substantially a rotation around a pivot axis.

Figure 4:
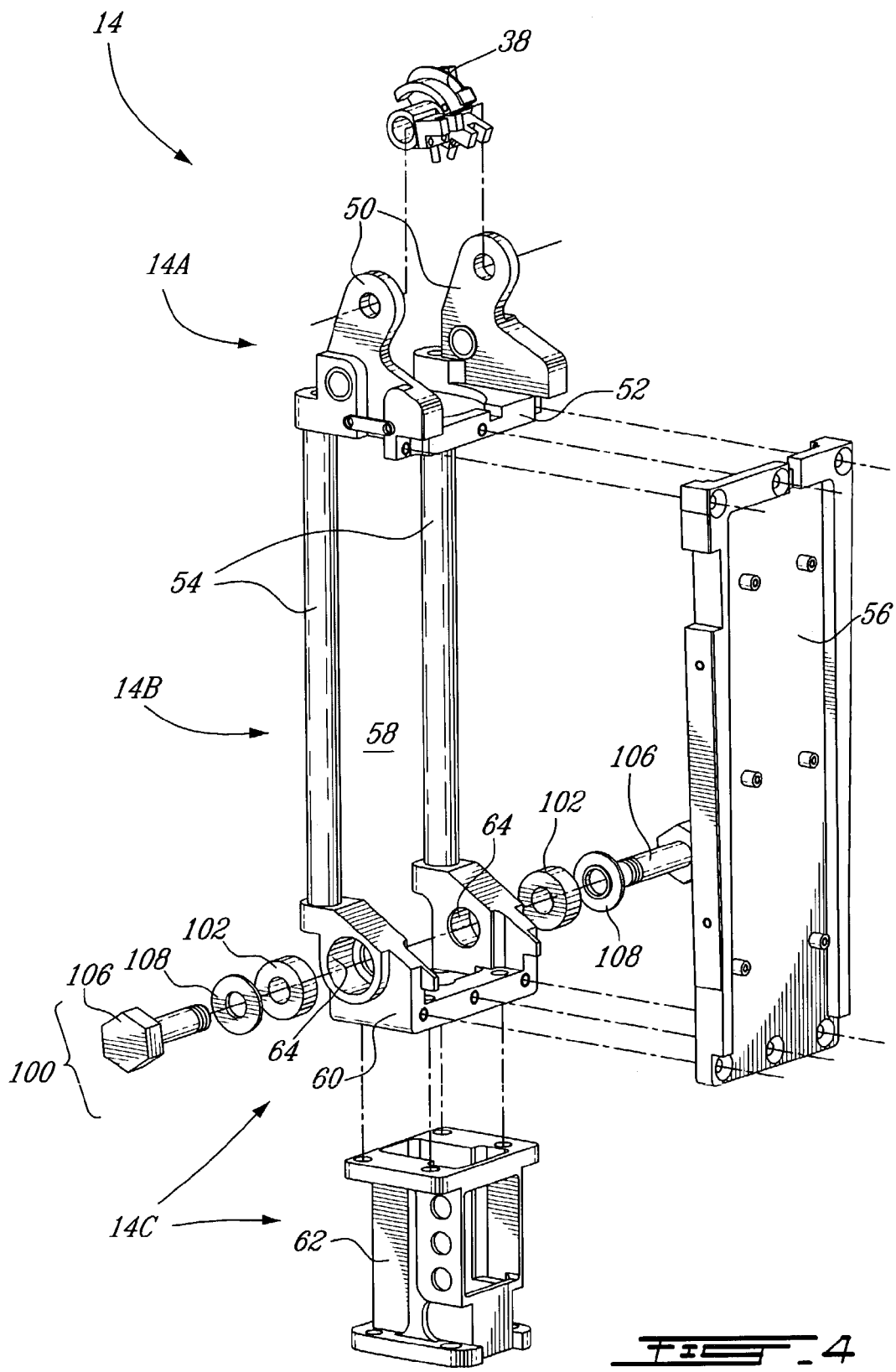
FIG. 4 is an exploded view of the trans-tibial member and the third pivot assembly shown in FIG. 1.
Figure 7:
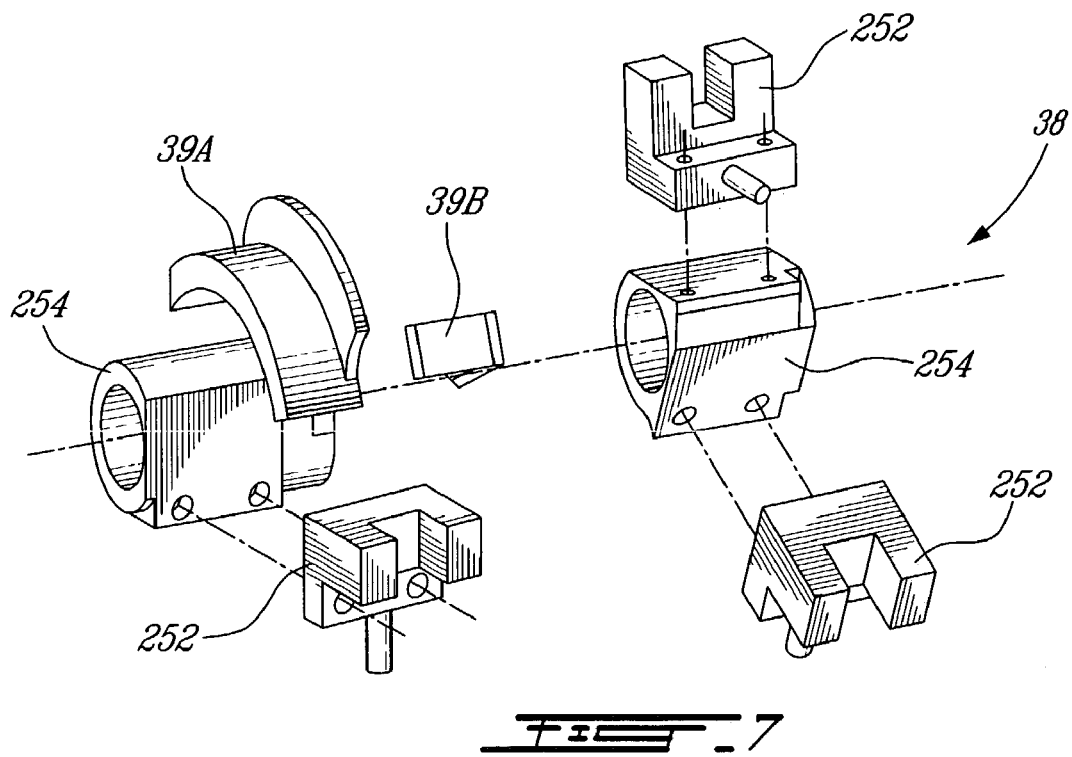
FIG. 7 is an exploded view of the optical switch support shown in FIG. 4.

In the preferred embodiment, the first pivot assembly (30) defines a first pivot axis (31) that is substantially perpendicular to a main longitudinal axis (15) extending along the length of trans-tibial member (14) in the frontal plane, as shown in FIG. 1. This first pivot assembly (30) also comprises an axle (32) supported by two bearings (34), each mounted in a corresponding housing (36) in the flanges (24) of the knee member (12). An example of bearing (34) is a single groove-bearing model 6300-ZZ manufactured by NSK Inc. Of course, other types of bearings (34) may be used as well. A 10 mm shoulder nut (37) and a set of external spacers (35) allow to retain the bearings (34) on threaded ends of the axle (32). An optical switch support (38), shown in FIGS. 2, 4 and 7, is mounted around the axle (32) between the two flanges (24) of the knee member (12). The support (38) is described later in the description.

Preferably, as best shown in FIG. 3, a set of energy absorption bumpers (44) is provided at the back side of the knee member (12) to prevent out of range motion. These bumpers (44) can be, for example, bumper model GBA-1 manufactured by Tecspak Inc. Of course, other types of bumpers (44) may be used as well. They are mounted on corresponding brackets (42) located on the side and the front of the upper plate (26) of the knee member (12). The brackets (42) are also used to support conectors (78) which are described later in the description.

FIG. 4 shows the trans-tibial member (14) in accordance with the preferred embodiment. It includes three main sections, namely an upper section (14A), a middle section (14B), and a bottom section (14C).

The upper section (14A) of the trans-tibial member (14) is preferably a fork-shaped item with two flanges (50) projecting from a mounting base (52). The mounting base (52) is rigidly connected to a pair of trans-tibial post bars (54). A back plate (56) is provided at the back. The pair of bars (54) and the back plate (56) are part of the middle section (14B). They are both connected to the bottom section (14C), which is itself a two-part item in the preferred embodiment. The first part (60) is a somewhat U-shaped part under which the second part (62) is attached. The second part (62) is an extension under which the artificial foot (20) is provided. The means for connecting the artificial foot (20) may comprise a set of threaded holes in which screws are inserted. Other types of connectors may be used.

The artificial foot (20) may be, for example, a standard 26 cm Trustep prosthetic foot manufactured by College Park Industries Inc. or Allurion model ALX5260 prosthetic foot manufactured by Ossur Inc. Other types of articulated or non-articulated artificial foot (20) may be used if the selected prosthetic foot provides approximately at least the same dynamical response as the ones mentioned here above. The design of the prosthesis (10) is modular and consequently, it can be adjusted to any morphology. The artificial foot (20) may have an exposed metal or composite structure. It may also have a cosmetic covering that gives it the appearance of a human ankle and foot.

The pair of bars (54) and the back plate (56) provide a space (58) in which most of the actuator (16) is located. The various electronic and electric components may also be attached on either sides of the back plate (56). This compact design allows to keep the overall dimensions within that of a normal human leg.

Figure 5:
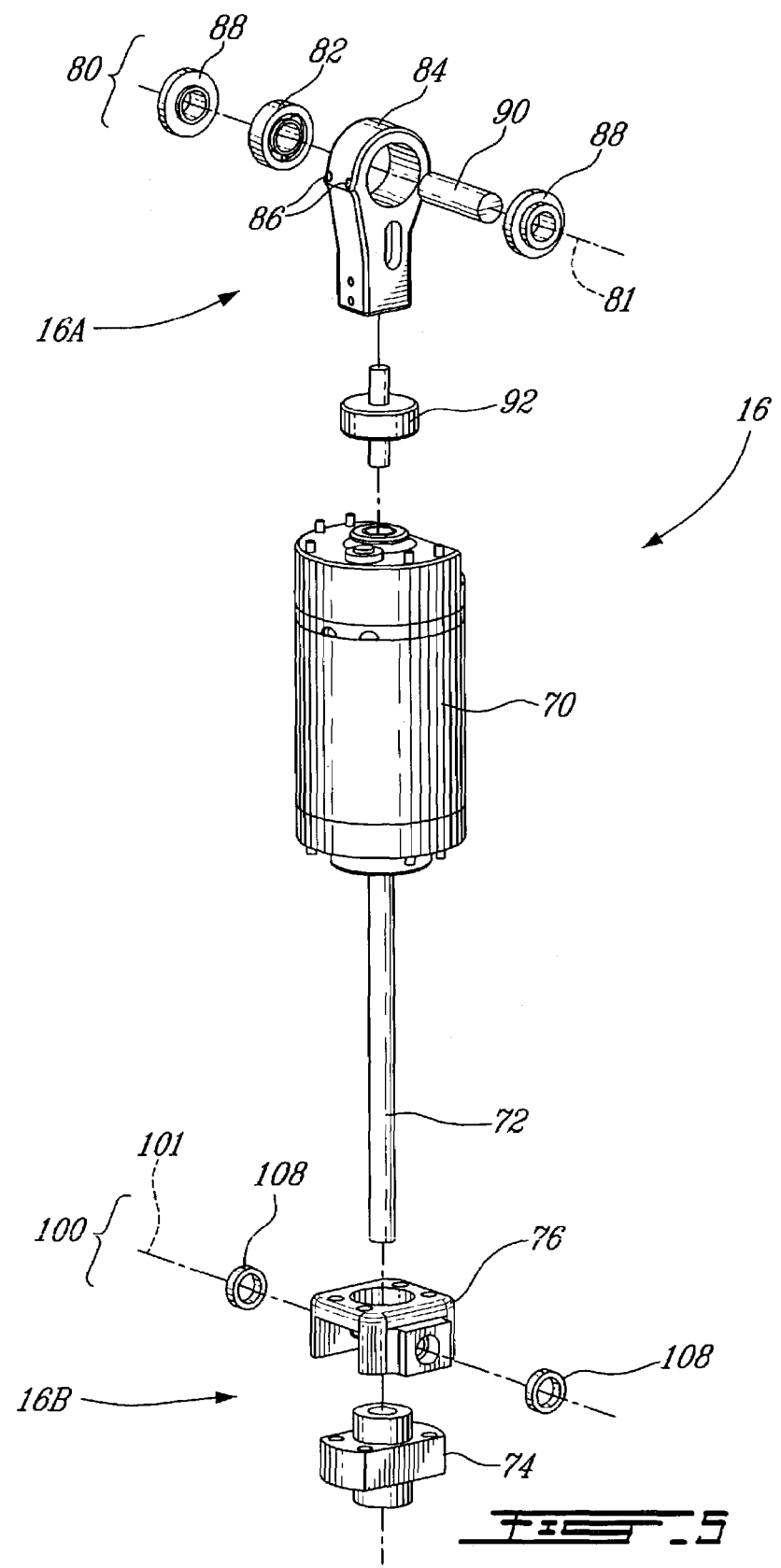
FIG. 5 is a partially exploded view of the linear actuator and the second pivot assembly shown in FIG. 1.

FIG. 5 shows the linear actuator (16) in accordance with the preferred embodiment. The upper end (16A) of the actuator (16) is connected to the knee member (12) and the bottom end (16B) is connected to the bottom section (14C) of the trans-tibial member (14). The function of the actuator (16) is to supply the prosthesis (10) with the necessary mechanical energy to execute, in a sagittal plane, the angular displacements synchronized with the amputee's locomotion. The linear motion of the actuator (16) is used to control the angle of the knee member (12) with reference to the trans-tibial member (14). The actuator (16) includes an electrical motor (70) coupled with a mechanism (72, 74) to transfer rotational motion into linear motion. An example of motor (70) is the model BN2328EU manufactured by Poly-Scientific. The motor (70) operates a screw (72) engaged to a fixed follower (74) at the bottom of the actuator (16). The follower (74) is held by a follower support (76). The follower (74) and the follower support (76) constitute the bottom end (16B) of the actuator (16). In use, when the motor (70) rotates, the screw (72) is rotated in or out of the follower (74). This pushes or pulls the knee member (12), thereby causing a relative rotation between the knee member (12) and the trans-tibial member (14).

The choice of the linear actuator (16) is primarily based on weight versus torque ratio and speed of available motor technologies. It is preferred over a direct drive system coupled directly to the knee member (12) because it takes less space for the torque requirement in human locomotion. It was found that ideally, the actuator (16) must be capable of supplying a continuous force of about 515 N and a peak force of about 2250 N.

Figure 6:
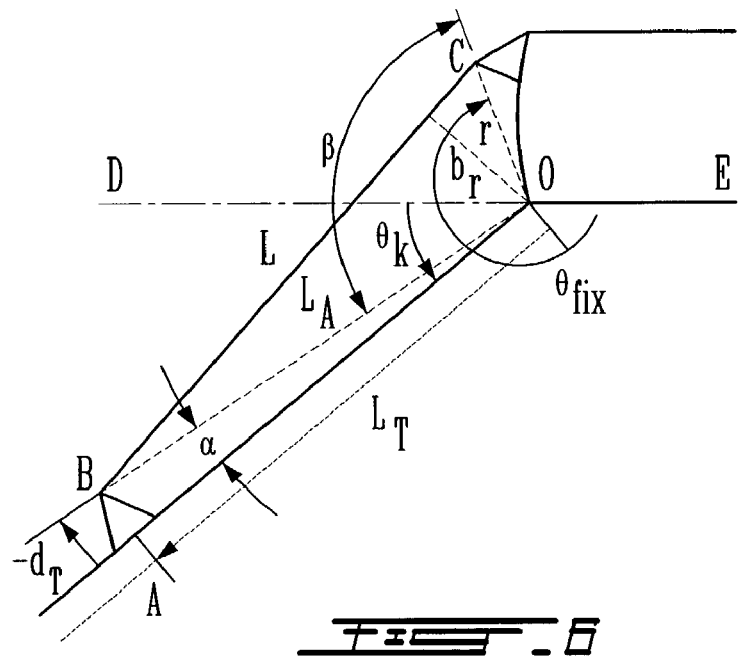
FIG. 6 is a diagram illustrating the geometrical model with the front actuator configuration.

The prosthesis (10) of the preferred embodiment further comprises a second pivot assembly (80). The second pivot assembly (80) operatively connects the upper end (16A) of the actuator (16) to the knee member (12). The second pivot assembly (80) defines a second pivot axis (81) that is substantially parallel to the first pivot axis (31). It is also spaced from the plane defined by its first pivot axis (31) and the main longitudinal axis (15). An example of this configuration is schematically illustrated in FIG. 6. This diagram represents the various pivot axes. The first pivot axis (31) is identified as "O". The second pivot axis (81) is identified with the letter "C". Both axes (C, O) are spaced apart by the distance "r". This distance creates a lever arm allowing the actuator (16) to move the trans-tibial member (14) with reference to the knee member (12).

FIG. 5 shows that the second pivot assembly (80) of the preferred embodiment comprises a bearing (82) inserted in a mechanical connector (84) forming the upper end (16A) of the actuator (16). The bearing (82) may be a needle bearing, for example needle bearing model NK14/16 manufactured by INA Inc. It is held in place by means of shoulder screws (86) and aluminum spacers (88). It was found that ideally, the bearing (82) must withstand a static charge up to about 11500 N (2600 lbf) and allows for a typical misalignment of 1 to 3°. The needle bearing (82) is preferred since it has practically no mechanical play and a low coefficient of friction when compared to bushing or rod ends. Of course, other types of bearings may be used as well. An axle (90) links the mechanical connector (84) to corresponding holes in the flanges (24) of the knee member (12). The mechanical connector (84) is secured over the motor (70) using a load cell (92), which is described later in the description.

The bottom end (16B) of the actuator (16) is operatively connected to the trans-tibial member (14) of the preferred embodiment using a third pivot assembly (100), as shown in FIGS. 4 and 5. The third pivot assembly (100) defines a third pivot axis (101) and also preferably comprises one or more needle bearings (102), each mounted in a corresponding housing (64) provided in the first part (60) of the bottom section (14C) of the trans-tibial member (14). Two standard needle bearings (102) may be used for that purpose, for example needle bearing model NK14/16 manufactured by INA Inc. Of course, other types of bearings may be used as well in the second (80) and the third pivot assembly (100). A set of screws (106) and spacers (108) completes the third pivot assembly (100).

The various structural parts of the prosthesis (10) are preferably made of a light material, for instance aluminum or a composite material, such as carbon fiber, fiberglass or the like. A particularly suitable material is thermally treated 6061T6 aluminum. The various parts are preferably screwed together, although they may be welded and otherwise secured together Screwing the parts together is preferred since this increases manufacturability, facilitates servicing and replacement of the parts, and usually improves the overall aesthetics.

FIG. 7 shows the specialized mechanical support (38) appearing in FIGS. 2 and 4. This specialized mechanical support (38) is used firstly to fix the optical switchs as explained hereafter. Secondly, the specialized mechanical support (38) is used to facilitate the transition between the part of a cable (not shown) between the relatively fixed section of the prosthesis (10) and the relatively movable section thereof. Connectors (78), attached to the brackets (42) of the knee member (12), provide the required connections. A similar connector (78) is provided on the motor (70). A two-part wire clamp (39A,39B) on parts (254) allows to hold the wire on the support (38).

Rear Actuator Configuration

FIGS. 8 to 13 show the prosthesis (10) in accordance with a second possible embodiment. This illustrates an example of a prosthesis (10) with a rear actuator configuration. This embodiment is very similar to the one using the front actuator configuration. It is illustrated with another kind of actuator (16) and another model of artificial foot (20). The middle section (14B) of the trans-tibial member (14) uses four bars (54) instead of two. It does not have a back plate. Moreover, no bottom extension is provided on the trans-tibial member (14).

The trans-tibial member (14) also has a shell type architecture composed, for example, of ½" trans-tibial post bars (54) linking together the knee member (12) and the artificial foot (20). In the illustrated embodiment, the actuator (16) could be a standar linear motor (FIG. 5) or a serial elastic actuator (SEA) (FIG. 8) equipped with a customized commercially available motor (70) although the prosthesis (10) is designed such that it can receive any type of linear actuator (16) of the same approximate size. The SEA actuator (16) (FIG. 8) has a ball screw transmission system including a screw (72) coupled with an elastic device (110) of known characteristics. This actuator (16) (FIG. 8) allows a force control actuation based on the deformation of elastic components. As well, the design allows energy storage, shock tolerance and relatively stable force control. The SEA actuator (16) (FIG. 8) was developed by Gill Pratt of the MIT Leg Laboratory and has been patented in 1997 as U.S. Pat. No. 5,650,704. In one implementation, it was provided with a Litton BN23-28 motor (70) and a ⅜" diameter with ⅛" pitch ball screw (72). The SEA actuator (16) (FIG. 8) is commercialized by Yobotic Inc.

Figure 13:
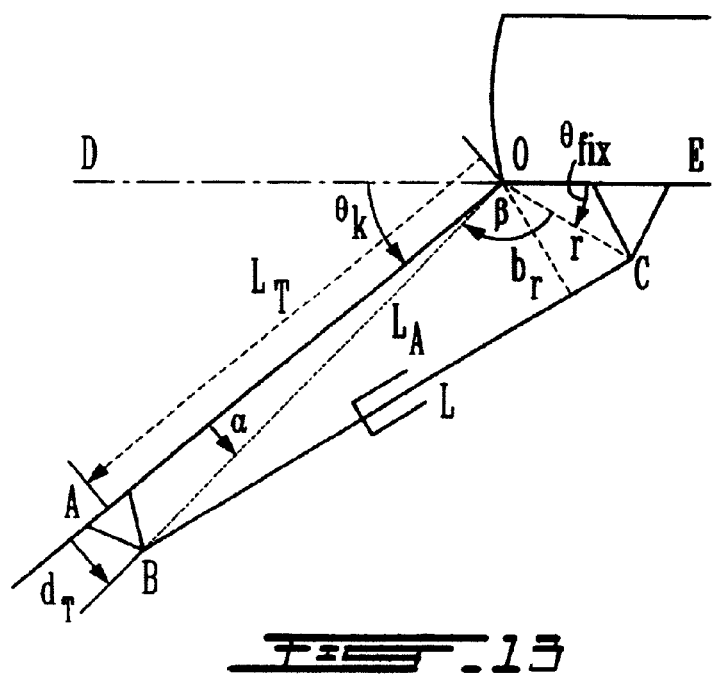
FIG. 13 is a diagram illustrating the geometrical model with the rear actuator configuration.

FIG. 13 illustrates the geometrical model of the rear actuator configuration. It is essentially similar to that of the front actuator configuration as shown in FIG. 6.

Control System

Figure 14:
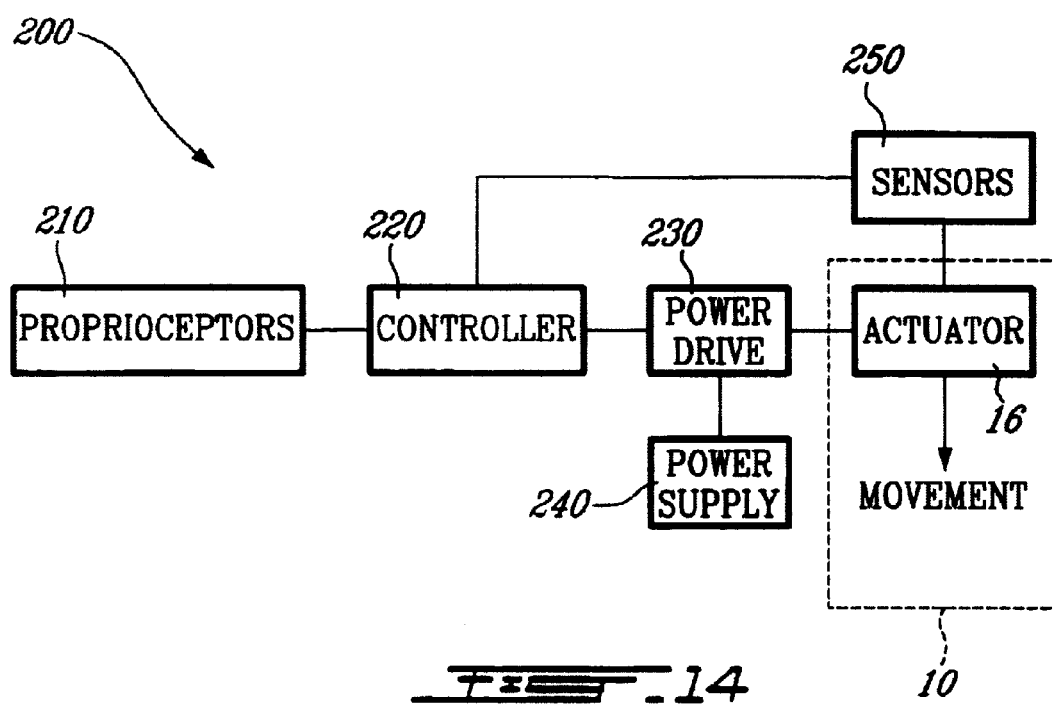
FIG. 14 is a bloc diagram showing an example of a control system for the actuator of the prosthesis.

FIG. 14 illustrates a control system (200) that can be used to operate the actuator (16) of the prosthesis (10). This figure first shows a set of artificial proprioceptors (210), which are sensors used to capture information in real time about the dynamics of the amputee's locomotion. The set of artificial proprioceptors (210) provide sensing information to a controller (220). The controller (220) determines the joint trajectories and the required forces that must be applied by the actuator (16). The set-point (joint trajectories and the required forces) is then sent to the actuator (16) via the power drive (230) itself connected to the power supply (240).

The power supply (240) can be, for example, a flexible battery pack belt such as the Lighting Powerbelt model, manufactured by Cine Power International Ltd. Other examples of power supply (240) are the battery model SLPB526495 manufactured by Worley Inc. and the super capacitors manufactured by Cap-XX. Examples of power drive (230) are the 5121 model, manufactured by Copley Controls Corps Inc. and the model BE40A8 manufactured by Advanced Motion Control. It should be noted that the design of the power supply (240) and that of the power drive (230) are not limited to the devices mentioned here above and could be performed by any custom or commercial products if the selected devices meet the electrical specification of the selected actuator (16) used with the prosthesis (10).

Preferably, the prosthesis (10) further includes a set of sensors (250) to provide feedback information to the controller (220). This feedback allows the controller (220) to adjust the forces and various other parameters. Examples of parameters that can be monitored are the relative angle of the knee member (12) and the torque at the knee member (12) being exerted by the actuator (16). Other types of measurements may be taken. The measurement of the relative angle of the knee member (12) can be taken, for example, by a standard commercially available incremental optical encoder (260) such as a reading head model EM1-0-250 and a Mylar® strip (262) marked with evenly spaced increments model LIN-250-16-S2037 manufactured by US Digital Inc. Others sensors used as limit switchs for the limitation of the angular motion of the prosthesis (10) are the optical switchs preferably mounted onto the specialized mechanical support (38). Cable connectors (78), shown in FIGS. 1 and 2, allow to link the external devices to internal components of the prosthesis (10).

The optical switches (252) are fixed on the first pivot axis (31) and are used to set the reference angular position of the knee member (12). Once this reference position is known, the optical encoder information is used to compute the knee member (12) angle via motor rotation, roller-screw pitch and prosthesis geometry. Moreover, the optical switches (252) are used to prevent out of range motion by sending a signal to the controller (220) when the knee member (12) approaches critical positions. Of course, the optical switches (252) may be use for other purposes according to the nature of the command associated with the switches detection. Another possible way of measuring the relative angle of the knee member (12) is by using a combination of an absolute optical encoder such as, for example, encoder model E2-512-250-I manufactured by US Digital Inc. and optical switches. An example of these switches is the switch model PM-L24 manufactured by SUNX.

The measurement of the torque is taken, for example, by a standard commercially available potentiometer measuring the compression of the elastic devices of the actuator (16) in the rear actuator configuration (FIG. 8), such as the conductive plastic resistance elements model PTN025 manufactured by Novotechnik Inc. The force being exerted by the actuator (16) may also be measured, as a load cell (92). An example of the load cell is the model LC 202 1K manufactured by Omegadyne. A connector on the motor (70) allows to link the internal sensor to the cable. It should be noted that the sensors (250) of the prosthesis (10) are not limited to the above-mentioned devices and can be performed by other suitable instruments.

EXAMPLE

Calculation for the Optimal Angle

One can assume the following technical specifications:
a geometrical volume corresponding to the anthropometrical volume of a natural shank of an individual having a weight of 70 kg and a height of 170 cm;
a maximal distance r set at 0.055 m, that is r<0.055 m;
a minimal and a maximal length $L_T$ set at 0.3 m and 0.4 m respectively, that is 0.3 m<$L_T$<0.4 m; and
a minimal and a maximal distance $d_T$ set at −0.015 m and +0.015 m, that is −0.015 m<$d_T$<+0.015 m.

The geometrical model can be defined with the following equations:

$$\beta = \pi - \theta_{fix} - \alpha - \theta_K \quad \text{Equation 1}$$

$$L_A = \sqrt{L_T^2 + d_T^2} \quad \text{Equation 2}$$

$$\alpha = \arctan\left(\frac{d_T}{L_T}\right) \quad \text{Equation 3}$$

$$L^2 = L_A^2 + r^2 - 2 \cdot L_A \cdot r \cdot \cos\beta \quad \text{Equation 4}$$

$$b_r = \frac{r \cdot L_A \cdot \sin\beta}{\sqrt{L_A^2 + r^2 - 2 \cdot L_A \cdot r \cdot \cos\beta}} \quad \text{Equation 5}$$

where
$\theta_K$ Knee angle, ∠DOA
r Distance between the center of rotation "O" of the knee member (12) and the attachment point of the actuator (16) on the knee member (12)
$\theta_{fix}$ Angle between r and the stump's center axis, ∠EOC
$L_A$ Distance between the center of rotation of the knee member (12) and the attachment point of the actuator (16) on the trans-tibial member (14) $\overline{OB}$
$L_T$ Length between the center of rotation of the knee member (12) and the attachment point of the trans-tibial member (14) $\overline{OA}$
$d_T$ Distance between the center axis of the trans-tibial member (14) and the actuator (16) attachment point of the trans-tibial member (14), $\overline{AB}$
α Angle formed between $L_T$, $L_A$: ∠AOB
L Length of the actuator (16), $\overline{BC}$
β Angle formed between $L_A$, r: ∠BOC
$b_r$ Lever arm of the actuator (16) versus the first pivot axis (31)

Preferably, the lever arm $b_r$ is assumed to be maximum at a knee angle $\theta_k$ of 35 degrees. The geometrical calculation of the mechanical design are based on the setting of the distance r, the length $L_T$, the distance $d_T$ and the angle $\theta_{fix}$. Therefore, these parameters are defined in accordance with the anthropomorphic measurements of the amputee and the selected actuator (16).

For an angle $\theta_{fix}$, the optimal value for a maximum lever arm $b_r$ is found when Equation 5 is at a maximum value, that is:

$$\frac{\partial b_r}{\partial \theta_{fix}} = 0 \qquad \text{Equation 6}$$

where $\theta_{fix} = \pi - \alpha - \theta_K - \beta$

This condition is reached for the configuration shown in FIGS. 6 and 13 when:

$$\beta = \pm \frac{3}{2}\pi \qquad \text{Equation 7}$$

From Equation 1, the optimal angle between distance r and the center axis of the socket, denoted $\theta_{fix}|_{optimal}$, is defined as:

$$\theta_{fix}|_{optimal} = \begin{bmatrix} +\pi/2 \\ -\pi/2 \end{bmatrix} - \theta_k - \alpha \qquad \text{Equation 8}$$

where $+\pi/2$ and $-\pi/2$ correspond to the rear and the front actuator configuration respectively.

The result is that the optimal angle $\theta_{fix}$ is preferably set at 125±3 degrees.

What is claimed is:

1. An actuated leg prosthesis for above-knee amputees, the prosthesis comprising:
    a knee member;
    first means for connecting a socket over the knee member;
    an elongated trans-tibial member having an upper end and a bottom end, the trans-tibial member defining a main longitudinal axis;
    second means for connecting an artificial foot under the bottom end of the trans-tibial member;
    a linear actuator having an upper end and a bottom end, the linear actuator including a motor coupled with a mechanism to impart a linear motion to the bottom end of the actuator with respect to the upper end of the actuator, thereby inducing extension or retraction of the linear actuator;
    third means for operatively connecting the trans-tibial member to the knee member;
    fourth means for operatively connecting the upper end of the actuator to the knee member; and
    fifth means for operatively connecting the bottom end of the actuator to the bottom end of the trans-tibial members;
    wherein extension or retraction of the linear actuator induces a corresponding rotation of the knee member relative to the elongated trans-tibial member.

2. The prosthesis according to claim 1, wherein:
    the third means comprise a first pivot assembly defining a first pivot axis that is perpendicular to the main longitudinal axis;
    the fourth means comprise a second pivot assembly defining a second pivot axis that is substantially parallel to the first pivot axis, the second pivot axis being spaced apart from the first pivot axis and the main longitudinal axis; and
    the fifth means comprise a third pivot assembly defining a third pivot axis that is substantially parallel to and spaced apart from the first pivot axis.

3. The prosthesis according to claim 1, wherein the trans-tibial member has a middle section comprising at least two spaced-apart bars, the bars generally defining a space in which most of the actuator is located.

4. The prosthesis according to claim 1, further comprising an artificial foot attached under the bottom end of the trans-tibial member, the artificial foot defining a front side and a rear side of the prosthesis.

5. The prosthesis according to claim 4, wherein the upper end of the actuator is connected to the front side of the prosthesis.

6. The prosthesis according to claim 5, wherein the trans-tibial member comprises a back plate extending between the upper end and the bottom end of the trans-tibial member.

7. The prosthesis according to claim 4, wherein the upper end of the actuator is connected to the rear side of the prosthesis.

8. The prosthesis according to claim 7, wherein the trans-tibial member has a middle section comprising at least two spaced-apart bars, the bars generally defining a space in which most of the actuator is located.

9. The prosthesis according to claim 4, further comprising a socket attached over the knee member.

10. The prosthesis according to claim 1, further comprising sixth means for controlling the actuator.

11. The prosthesis according to claim 10, wherein the sixth means comprise a controller outputting control signals in response to input signals from proprioceptors.

12. The prosthesis according to claim 11, wherein the controller has an output connected to a power drive, the power drive supplying electrical energy to the actuator, coming from a power source, in response to the control signals.

13. The prosthesis according to claim 11, wherein the input signals further comprise signals from sensors mounted on the prosthesis and located outside the prosthesis.

14. An actuated leg prosthesis for above-knee amputees, the prosthesis comprising:
    a knee member;
    a socket connected over the knee member;
    an elongated trans-tibial member having an upper end and a bottom end, the trans-tibial member defining a main longitudinal axis;
    an artificial foot connected under the bottom end of the trans-tibial member, the artificial foot defining a front side and a rear side of the prosthesis;
    a linear actuator having an upper end and a bottom end, the linear actuator including a motor coupled with a mechanism to impart a linear motion to the bottom end of the linear actuator with respect to the upper end of the linear actuator, thereby inducing extension or retraction of the linear actuator;
    a first pivot assembly to operatively connect the trans-tibial member to the knee member, the first pivot assembly defining a first pivot axis that is perpendicular to the main longitudinal axis;

a second pivot assembly to operatively connect the upper end of the actuator to the knee member, the second pivot assembly defining a second pivot axis that is substantially parallel to the first pivot axis, the second pivot axis being spaced apart from the first pivot axis and the main longitudinal axis; and a third pivot assembly to operatively connect the bottom end of the actuator to the bottom end of the trans-tibial member, the third pivot assembly defining a third pivot axis that is substantially parallel to and spaced apart from the first pivot axis;

wherein extension or retraction of the linear actuator induces a corresponding rotation of the knee member relative to the elongated trans-tibial member.

15. The prosthesis according to claim 14, wherein the trans-tibial member has a middle section comprising at least two spaced-apart bars, the bars generally defining a space in which most of the actuator is located.

16. The prosthesis according to claim 14, wherein the upper end of the actuator is connected to the front side of the prosthesis.

17. The prosthesis according to claim 16, wherein the trans-tibial member comprises a back plate extending between the upper end and the bottom end of the trans-tibial member.

18. The prosthesis according to claim 14, wherein the upper end of the actuator is connected to the rear side of the prosthesis.

19. The prosthesis according to claim 18, wherein the trans-tibial member has a middle section comprising at least two spaced-apart bars, the bars generally defining a space in which most of the actuator is located.

20. The prosthesis according to claim 14, further comprising a controller to control the actuator, the controller outputting control signals in response to input signals from proprioceptors.

21. The prosthesis according to claim 20, wherein the controller has an output connected to a power drive, the power drive supplying electrical energy to the actuator, coming from a power source, in response to the control signals.

22. The prosthesis according to claim 20, wherein the input signals further comprise signals from sensors mounted on the prosthesis and located outside the prosthesis.

23. An actuated leg prosthesis for above-knee amputees, the prosthesis comprising:

a knee member;

a socket connected over the knee member;

an elongated trans-tibial member having an upper end and a bottom end, the trans-tibial member defining a main longitudinal axis;

an artificial foot connected under the bottom end of the trans-tibial member, the artificial foot defining a front side and a rear side of the prosthesis;

a linear actuator having an upper end and a bottom end, the linear actuator including an electrical motor coupled with a mechanism to transfer the rotational motion of the electrical motor into linear motion of the bottom end of the linear actuator with respect to the upper end of the linear actuator, thereby inducing extension or retraction of the linear actuator;

a first pivot assembly to operatively connect the trans-tibial member to the knee member, the first pivot assembly defining a first pivot axis that is perpendicular to the main longitudinal axis;

a second pivot assembly to operatively connect the upper end of the actuator to the knee member, the second pivot assembly defining a second pivot axis that is substantially parallel to the first pivot axis, the second pivot axis being spaced apart from the first pivot axis and the main longitudinal axis; and a third pivot assembly to operatively connect the bottom end of the actuator to the bottom end of the trans-tibial member, the third pivot assembly defining a third pivot axis that is substantially parallel to and spaced apart from the first pivot axis;

wherein extension or retraction of the linear actuator induces a corresponding rotation of the knee member relative to the elongated trans-tibial member.

24. The prosthesis according to claim 23, wherein the mechanism includes a screw engaged to a follower at the bottom end of the linear actuator and wherein rotation of the electrical motor rotates the screw in or out of the follower causing a relative rotation between the knee member and the trans-tibial member.

* * * * *